(12) United States Patent
Abi Aoun et al.

(10) Patent No.: US 12,171,260 B2
(45) Date of Patent: Dec. 24, 2024

(54) AEROSOL GENERATION

(71) Applicant: NICOVENTURES TRADING LIMITED, London (GB)

(72) Inventors: Walid Abi Aoun, London (GB); Sally Bell, London (GB)

(73) Assignee: NICOVENTURES TRADING LIMITED, London (GB)

( * ) Notice: Subject to any disclaimer, the term of this patent is extended or adjusted under 35 U.S.C. 154(b) by 545 days.

(21) Appl. No.: 17/420,467

(22) PCT Filed: Dec. 20, 2019

(86) PCT No.: PCT/GB2019/053653
§ 371 (c)(1),
(2) Date: Jul. 2, 2021

(87) PCT Pub. No.: WO2020/141314
PCT Pub. Date: Jul. 9, 2020

(65) Prior Publication Data
US 2022/0079223 A1    Mar. 17, 2022

(30) Foreign Application Priority Data
Jan. 4, 2019   (GB) ..................................... 1900125

(51) Int. Cl.
| A24F 40/10 | (2020.01) |
| A24B 15/167 | (2020.01) |
| A24F 40/20 | (2020.01) |
| A24F 40/30 | (2020.01) |
| A24F 40/42 | (2020.01) |

(52) U.S. Cl.
CPC ............ *A24F 40/30* (2020.01); *A24B 15/167* (2016.11); *A24F 40/10* (2020.01); *A24F 40/20* (2020.01); *A24F 40/42* (2020.01)

(58) Field of Classification Search
CPC .......... A24F 40/00; A24F 40/10; A24F 40/20; A24F 40/30; A24F 40/40; A24F 40/42; A24B 15/10; A24B 15/16; A24B 15/167
USPC ......................................................... 131/329
See application file for complete search history.

(56) References Cited

U.S. PATENT DOCUMENTS

| 4,284,089 A | 8/1981 | Ray |
| 4,907,606 A | 3/1990 | Lilja et al. |
| 5,105,834 A | 4/1992 | Saintsing et al. |
| 8,356,606 B2 | 1/2013 | Sengupta et al. |
| 2012/0006342 A1 | 1/2012 | Rose et al. |

(Continued)

FOREIGN PATENT DOCUMENTS

| EP | 2399637 A1 | 12/2011 |
| GB | 2561266 | 10/2018 |

(Continued)

OTHER PUBLICATIONS

International Search Report and Written Opinion for PCT/GB2019/053653 date mailed Mar. 17, 2020.

*Primary Examiner* — Khiem M Nguyen
(74) *Attorney, Agent, or Firm* — WOMBLE BOND DICKINSON (US) LLP

(57) ABSTRACT

An aerosol-generating article comprising an aerosolizable material comprising nicotine; a solid basic material; and a wetting agent; wherein in use, the wetting agent is combined with the solid basic material and the aerosolizable material on actuation of a combining mechanism by a user.

17 Claims, 2 Drawing Sheets

(56) References Cited

U.S. PATENT DOCUMENTS

| | | | |
|---|---|---|---|
| 2012/0312314 A1 | 12/2012 | Plakidis et al. | |
| 2013/0160779 A1 | 6/2013 | Chida et al. | |
| 2013/0160780 A1 | 6/2013 | Matsumoto et al. | |
| 2016/0205992 A1 | 7/2016 | Bell et al. | |
| 2017/0319799 A1 | 11/2017 | Yamada et al. | |
| 2017/0360099 A1 | 12/2017 | Duc | |
| 2018/0279666 A1 | 10/2018 | Aoun et al. | |
| 2018/0279667 A1 | 10/2018 | McAdam et al. | |
| 2022/0079223 A1* | 3/2022 | Abi Aoun | A61K 31/465 |
| 2023/0250590 A1* | 8/2023 | Zitturi | A24D 1/02 162/135 |

FOREIGN PATENT DOCUMENTS

| | | |
|---|---|---|
| KR | 20180111460 | 10/2018 |
| RU | 2675474 C1 | 12/2018 |
| WO | 2007/054167 A1 | 5/2007 |
| WO | WO2010107613 | 9/2010 |
| WO | 2011/034723 A1 | 3/2011 |
| WO | 2016/050244 A1 | 4/2016 |
| WO | 2016/079729 A1 | 5/2016 |
| WO | WO2016124780 | 8/2016 |
| WO | 2017/029151 A1 | 2/2017 |
| WO | WO2017081487 | 5/2017 |
| WO | 2017/220340 A1 | 12/2017 |
| WO | 2018/033649 A1 | 2/2018 |
| WO | 2018/224132 A1 | 12/2018 |

\* cited by examiner

AEROSOL GENERATION

PRIORITY CLAIM

The present application is a National Phase entry of PCT Application No. PCT/GB2019/053653, filed Dec. 20, 2019 which claims priority from GB Patent Application No. 1900125.4 filed Jan. 4, 2019, each of which is hereby fully incorporated herein by reference.

TECHNICAL FIELD

The present invention relates, without limitation, to an aerosol-generating article, an aerosol generating assembly, a kit and a method of generating an inhalable medium.

BACKGROUND

Smoking articles such as cigarettes, cigars and the like burn tobacco during use to create tobacco smoke. Alternatives to these types of articles release compounds without burning to form an inhalable medium, and may be referred to as aerosol generating devices.

Examples of such products are heat-not-burn devices, also known as tobacco heating products and tobacco heating devices. In such devices, a solid aerosolizable material, which may or may not contain tobacco, is heated, without burning, to form an inhalable medium. Components of the solid aerosolizable material are volatilized to form a vapor and/or aerosol. The inhalable medium may, in some cases, comprise nicotine.

Further examples of such products are heating devices include e-cigarette/heat-not-burn hybrid devices, also known as electronic tobacco hybrid devices or just hybrid devices. These hybrid devices contain a vapor or aerosol precursor (such as a liquid or gel) which is vaporized by heating to produce a vapor or aerosol. The vapor precursor may contain flavorings and/or aerosol-generating substances, such as glycerol and in some instances, nicotine. The vapor or aerosol passes through a substrate material in the device and entrains one or more constituents of that substrate material to produce the inhaled medium. The substrate material may be, for example, tobacco, other non-tobacco products or a combination, such as a blended mix, which may or may not contain nicotine.

SUMMARY

In some embodiments described herein, the disclosure provides an aerosol-generating article comprising; (i) an aerosolizable material comprising nicotine; (ii) a solid basic material; and (iii) a wetting agent; wherein in use, the wetting agent is combined with the solid basic material and the aerosolizable material on actuation of a combining mechanism by a user.

In some embodiments, the disclosure provides an aerosol generating assembly comprising a heater and an aerosol-generating article according to other embodiments of the disclosure.

In some embodiments, the disclosure provides a kit comprising an aerosol-generating article according to other embodiments of the disclosure, and a device for use in generating an inhalable medium, wherein the device comprises a heater.

The disclosure also provides a method of generating an inhalable medium comprising; combining a wetting agent with a composition, the composition comprising a solid basic material and an aerosolizable material comprising nicotine, to release nicotine from the aerosolizable material, and volatilizing components of the aerosolizable material to form an inhalable medium.

The disclosure also provides a method of providing sustained release of nicotine from an aerosolizable material comprising nicotine, the method comprising; providing a wetting agent and a composition comprising a solid basic material and the aerosolizable material; combining the wetting agent and the composition, thereby forming a basic solution; and liberating nicotine from the aerosolizable material.

The disclosure also provides the use of a wetting agent to provide sustained nicotine delivery from an aerosolizable material comprising nicotine, wherein the aerosolizable material is mixed with a solid basic material, and wherein the wetting agent is contacted with the solid basic material and the aerosolizable material, resulting in the release of nicotine from the aerosolizable material, wherein components of the aerosolizable material are volatilized to form an inhalable medium The disclosure also provides a cartridge for use in a device for containing an inhalable medium, the cartridge containing a solid basic material and an aerosolizable material comprising nicotine, wherein the cartridge is configured for use in a device which contains a reservoir of a wetting agent.

Further features and advantages of the invention will become apparent from the following description of preferred embodiments of the invention, given by way of example only, which is made with reference to the accompanying drawings.

BRIEF DESCRIPTION OF THE DRAWINGS

Examples of devices for generating an inhalable medium according to the disclosure are described below with reference to the accompanying drawings, in which:

FIG. 4 shows a schematic longitudinal cross-sectional view of an example of a cartridge having a liquid container and an integral container for solid material; and.

DETAILED DESCRIPTION

Figure 1:
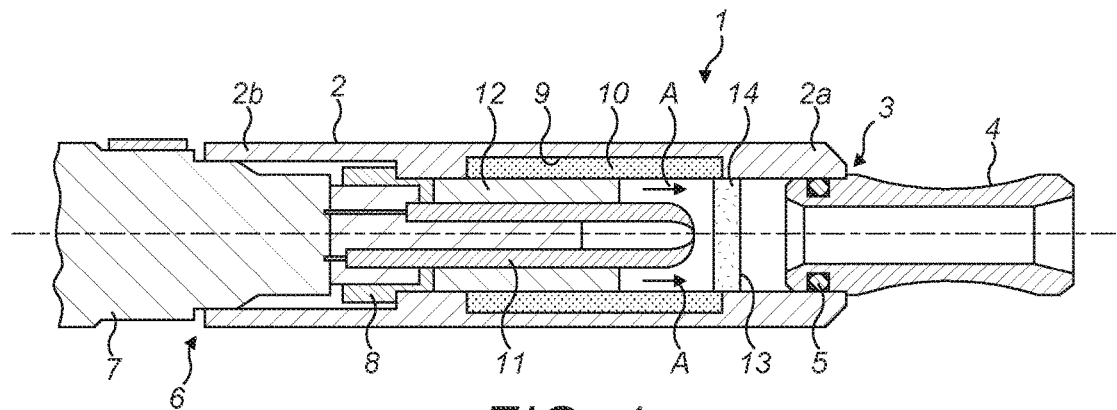
FIG. 1 shows a schematic longitudinal cross-sectional view of an example of a device for generating an inhalable medium.

Tobacco can be treated with base and water in order to ease liberation of nicotine from the tobacco. Nicotine is liberated from nicotine salts in tobacco by reaction with the base. Nicotine is then volatilized at a lower temperature in use.

The inventors have determined that if base-treated tobacco is used in known electronic tobacco hybrid devices, nicotine delivery per puff significantly drops during use. The reaction between base and nicotine occurs quickly; the pH-treated nicotine is then is liberated quickly and delivery during consumption may reduce from puff to puff. The inventors have also observed that nicotine from base-pH-treated tobacco may be lost from the device prior to use due to its high volatility.

The present disclosure provides improved consistency of nicotine delivery per puff through delaying pH-treatment of the aerosolizable material that contains nicotine (such as a tobacco material). The disclosure uses a wetting agent and a separate solid basic material alongside the aerosolizable material; in use the wetting agent and solid basic material are combined by the user, forming a basic solution which contacts the aerosolizable material and liberates nicotine. In some cases, the rate at which wetting agent contacts the solid basic material is controlled in use, thereby controlling the rate of nicotine liberation by the pH treatment. Prior to combination of the wetting agent, the solid basic material and the aerosolizable material containing nicotine, there is no basic pH treatment of the nicotine.

Moreover, basic pH treatment of tobacco results in the liberation of ammonia. Control of the rate of basic pH treatment controls the rate of release of ammonia, and this can improve the organoleptic properties of the tobacco (since the smell of ammonia is less strong).

In some embodiments described herein, the disclosure provides an aerosol-generating article comprising; (i) an aerosolizable material comprising nicotine; (ii) a solid basic material; and (iii) a wetting agent; wherein in use, the wetting agent is combined with the basic material and the aerosolizable material on actuation of a combining mechanism by a user.

The aerosolizable material is typically solid. In some cases, the aerosolizable material comprises a tobacco material. As used herein, the term "tobacco material" refers to any material comprising tobacco or derivatives therefore. The term "tobacco material" may include one or more of tobacco, tobacco derivatives, expanded tobacco, reconstituted tobacco or tobacco substitutes. The tobacco material may comprise one or more of ground tobacco, tobacco fiber, cut tobacco, extruded tobacco, tobacco stem, reconstituted tobacco, agglomerated tobacco, spheronised tobacco and/or tobacco extract.

In some cases, the aerosolizable material, such as tobacco, has a water content of 15 wt % or less, suitably 10 wt % or less. This ensures that reaction between moisture present in the aerosolizable material and the solid basic material is minimized.

The tobacco used to produce tobacco material may be any suitable tobacco, such as single grades or blends, cut rag or whole leaf, including Virginia and/or Burley and/or Oriental. It may also be tobacco particle 'fines' or dust, expanded tobacco, stems, expanded stems, and other processed stem materials, such as cut rolled stems. The tobacco material may be a ground tobacco or a reconstituted tobacco material. The reconstituted tobacco material may comprise tobacco fibers, and may be formed by casting, a Fourdrinier-based paper making-type approach with back addition of tobacco extract, or by extrusion.

The aerosolizable material may additionally comprise flavorings and/or aerosol generating agents.

The aerosolizable material may additionally comprise one or more casings, such as invert sugar, molasses, cane sugar, honey, cocoa, liquorice, polyols such as glycerol and propylene glycol and acids such as malic acid.

The aerosolizable material may additionally comprise one or more binders, such as alginates, celluloses or modified celluloses, starches or modified starches, or natural gums. In some embodiments, the aerosolizable material comprises an alginate such as sodium alginate, calcium alginate, potassium alginate or ammonium alginate.

The aerosolizable material may additionally comprise one or more fillers. Suitably, the filler may comprise an inorganic material such as calcium carbonate, perlite, vermiculite, diatomaceous earth, colloidal silica, magnesium oxide, magnesium sulphate and magnesium carbonate. In some cases, the filler comprises chalk. Suitably, the filler may comprise an organic material such as wood pulp, cellulose and cellulose derivatives.

In some cases, the aerosolizable material and the solid basic material are provided as a mixture, suitably a homogenous mixture. In some cases, the density of the solid basic material may be within about 10% or 5% of the density of the aerosolizable material to minimize separation of these components in the mixture.

In some cases, the weight ratio of solid basic material to aerosolizable material, calculated on a dry weight basis, may be in the range of about 0.05:1 to about 0.15:1, suitably 0.05:1 to 0.1:1.

In other cases, the solid basic material may be provided separately from the aerosolizable material, wherein the solid basic material is provided upstream of the aerosolizable material (wherein upstream refers to the direction of aerosol flow in use). In such cases, the solid basic material may be provided in a separate chamber to the aerosolizable material, or both components may be provided in the same chamber with the solid basic material provided at the upstream end.

As used herein, the term "solid basic material" refers to any material which forms a basic solution on dissolution in the wetting agent. Suitably, the material forms a basic solution which has a pH of greater than about 8. Suitably, the material forms a basic solution which has a pH of less than about 10. Suitably, the material forms a basic solution which has a pH of between about 8 and 9. In some cases, the solid basic material comprises sodium hydroxide, potassium hydroxide, calcium hydroxide, sodium hydrogen carbonate, potassium hydrogen carbonate, sodium carbonate, potassium carbonate, calcium carbonate or mixtures thereof.

In some cases, the wetting agent comprises an aerosol generating agent and/or water. In some cases, the wetting agent comprises at least one of water, glycerol and propylene glycol.

In some cases, the combining of the wetting agent with the solid basic material and the aerosolizable material comprising nicotine is puff-actuated. This means that that pH-treatment of the aerosolizable material only occurs during puffing, and nicotine liberation is minimized between puffs (reducing unintended nicotine losses and providing sustained nicotine delivery during the consumption period). That is, in some cases, the aerosol-generating article is configured for use in an aerosol generating device that comprises a puff detector.

In some cases, the wetting agent is encapsulated, and the capsule is ruptured in use to release the wetting agent so that it is combined with the solid basic material. In some such cases, the capsule may be crushable and release of the wetting agent is effected by the user crushing the capsule in use. In some such cases, the capsule may be ruptured by a piercing member. In one case, the piercing member may be moved into contact with the capsule by the user; for example, such movement may be button actuated. In another case, the piercing member may be provided as part of a device which the article is inserted into, wherein the piercing member ruptures the capsule as the article is inserted. In yet further cases, the wetting agent may be encapsulated by an encapsulating material that melts, decomposes, reacts, degrades, swells, dissolves or deforms to release the wetting agent at a temperature above room temperature but at or below the temperature reached during use. For example, the wetting agent may be encapsulated by an encapsulating material selected from a polysaccharide or cellulosic barrier material, a gelatin, a gum, a gel, a wax or a mixture thereof. In some cases, the encapsulating material is selected from one or more of alginates, dextran, maltodextrin, cyclodextrin, pectin, methyl cellulose, ethyl cellulose, hydroxyethyl cellulose, hydroxypropyl cellulose, carboxymethyl cellulose, cellulose ethers, gum Arabic, gum ghatti, gum tragacanth, Karaya, locust bean, acacia gum, guar, quince seed, xanthan gums, agar gel, agarose gel, carrageenans, furoidan, furcellaran and carnauba wax.

In some cases, wherein the wetting agent is heated to form a vapor and/or aerosol in use, and wherein the vapor and/or aerosol flows into contact with the solid basic material in use. For example, the article may be configured for use in an electronic tobacco hybrid device; the wetting agent may be provided as a component of a vapor or aerosol precursor (such as a liquid or gel) which is vaporized by heating to produce a vapor and/or aerosol. The assembly is configured to flow the vapor and/or aerosol into contact with the solid basic material and the aerosolizable material. The flowing vapor/aerosol containing a wetting agent dissolves the solid basic material to form a basic solution, which pH-treats the aerosolizable material, thereby liberating nicotine. In some cases, volatilization of the wetting material is puff-actuated. This means that that pH-treatment of the aerosolizable material only occurs during puffing, and nicotine liberation is minimized between puffs (reducing unintended nicotine losses and providing sustained nicotine delivery during the consumption period).

In some cases, the wetting agent is pumped into contact with the basic material on actuation of the pump by the user. The pump may be provided as part of an aerosol generating device into which the aerosol-generating article is inserted. In some such cases, the pump may be, for example, button actuated, so that the user controls the rate of pH treatment of the aerosolizable material, and thereby controls the rate of nicotine release. In some other cases, the pump may be puff actuated, so that pH-treatment of the aerosolizable material only occurs during puffing, and nicotine liberation is minimized between puffs (reducing unintended nicotine losses and providing sustained nicotine delivery during the consumption period).

The aerosol generating article may be provided as one component, or may be provided as more than one component. For example, the wetting agent may be provided in a first component, such as in a liquid pod for use in an electronic tobacco hybrid device, and the aerosolizable material and the solid basic material may be provided together in a second component, such as in a tobacco pod for use in an electronic tobacco hybrid device. The components may be clip together in some instances for insertion into a device. In some instances, the separate components may be inserted into the device individually.

The disclosure also provides an aerosol generating assembly comprising a heater and an aerosol-generating article according to embodiments of the disclosure.

In an embodiment, the heater is battery-operated. In an embodiment, the or each heater is an electrically resistive heater.

In some cases, the assembly may be a heat-not-burn assembly, in which the aerosolizable material is heated in use to generate an inhalable medium.

In some cases, the assembly may be an electronic tobacco hybrid assembly. In some such cases, the wetting agent may be provided as a component of a first volatilizable material. On heating of this material, the volatilizable material is volatilized and forms an aerosol and/or vapor comprising the wetting agent. The aerosol and/or vapor flows through the assembly and contacts the aerosolizable material and the solid basic material to liberate nicotine. On some other cases, the wetting agent may be included in an electronic tobacco hybrid assembly in other ways discussed herein, such as in encapsulated form.

In some particular cases, the disclosure provides an assembly comprising;
  a container retaining a first volatilizable material, the first volatilizable material comprising the wetting agent;
  a heater for volatilizing the first volatilizable material held in the container;
  a chamber containing an aerosolizable material comprising nicotine, and a solid basic material; and
  an outlet;
  the arrangement being such that in use, the first volatilizable material comprising the wetting agent is volatilized by the heater to form a vapor and/or an aerosol, which passes through the chamber containing the aerosolizable material and the solid basic material, and entrains one or more constituents of the aerosolizable material, thereby forming an inhalable medium which passes through the outlet.

In some cases, the first volatilizable material comprises a liquid or gel. The first volatilizable material may alternatively be referred to as a vapor/aerosol precursor. Suitably, the first volatilizable material comprises, substantially consists of or consists of a liquid. Suitable liquids include components conventionally used in e-cigarette liquids.

The first volatilizable material may comprise aerosol generating agents, such as propylene glycol and/or glycerol. Additionally, it may in some cases comprise flavorings. The material is typically volatilized at around 150-250° C.

In some cases, the aerosolizable material and/or the solid basic material may be porous, such that an aerosol or vapor can pass through the material. This provides a high contact area for the material to contact the aerosol and/or vapor.

Suitably, the aerosolizable material (prior to use) may have a pH of less than about 7, as measured according to the CORESTA protocol for measuring the pH of tobacco.

The first volatilizable material may comprise aerosol-generating agents, such as propylene glycol and/or glycerol. Additionally, it may in some cases comprise flavorings. The material is typically volatilized at around 150-250° C.

In some cases, the assembly heats the aerosolizable material in use, encouraging release of components thereof into the inhaled medium. In some cases, one heater may heat both the first volatilizable material and the aerosolizable material. In some cases, a second heater may be provided which heats the aerosolizable material. In some cases, the device does not heat the aerosolizable material, relying on heat carried by the vapor/aerosol to warm the material (thereby volatilizing components of the material which are then entrained in the vapor/aerosol flow).

In an embodiment, the assembly comprises a cooler or cooling zone downstream of the heater and upstream of the chamber containing the aerosolizable material, the cooler or cooling zone being arranged to cool vaporized material to form an aerosol of liquid droplets which in use passes through the aerosolizable material chamber. The cooler may be arranged in effect to act as a heat exchanger, allowing for recovery of heat from the vapor. The recovered heat can be used for example to pre-heat the aerosolizable material and/or to assist in heating the first volatilizable material.

In an embodiment, the heater is puff actuated. That is, the device includes a puff-detector and only heats the first volatilizable material on detection of a puff. This means that vapor/aerosol forms in the device only during puffs, thereby ensuring that pH-treatment of the tobacco material only occurs during puffing. This further delays pH treatment of the tobacco, reducing unintended nicotine losses and providing sustained nicotine delivery during the consumption period.

In an embodiment, the container holding the first volatilizable material is removable. The container may be in the form of a pot or the like (which in some embodiments may be annular for example), and/or an absorbent wadding or the like. The container may in effect be a disposable item which is replaced as a whole after use. As an alternative, the arrangement may be such that the user removes the container from the device, replaces used volatilizable material or tops up the material in the container, and then places the container back in the device.

In some cases, the container may be non-removable from the device. In such an embodiment, the user may just replace used material or top up material in the container after use as necessary.

In some cases, the container and the chamber are an integral unit. In some cases, the integral unit is a cartridge that can be removed from the device. Such a unit is an aerosol-generating article according to embodiments of the disclosure.

In some cases, the chamber is removable from the device. The chamber may be, for example, in the form of a cartridge or the like which contains the aerosolizable material (and optionally, the solid basic material) before use. The whole chamber containing the aerosolizable material (and optionally, the solid basic material) may in effect be a disposable item which is replaced as a whole after use. As an alternative, the arrangement may be such that the user removes the chamber from the device, replaces used material in the chamber, and then places the chamber back in the device.

The disclosure also provides a cartridge for use in a device for containing an inhalable medium, the cartridge containing a solid basic material and an aerosolizable material comprising nicotine, wherein the cartridge is configured for use in a device which contains a reservoir of a wetting agent. Suitably, the cartridge may be adapted for use in the device for generating an inhalable medium described herein.

The disclosure also provides a kit comprising an aerosol-generating article according to embodiments of the disclosure, and a device for use in generating an inhalable medium, wherein the device comprises a heater. Features described above in relation to the assembly are explicitly disclosed in combination with the kit aspect of the disclosure; features described in relation to the assembly may be features of the device. Thus, for example, the device may include one or more of a puff actuator, a cooling element or cooling zone, actuation means such as a button, further heaters, a pump for the wetting agent, and so on.

To the extent that they are compatible, features described in relation to the aerosol generating assembly are explicitly disclosed in combination with the aerosol-generating article and vice versa. Similarly, the features described in relation to the aerosol generating assembly or the aerosol-generating article explicitly disclosed in combination with the cartridge and vice versa.

Specifically, features of the aerosolizable material, the solid basic material and the wetting agent described herein are explicitly disclosed in combination with each embodiment of the disclosure (to the extent that they are compatible).

Examples of devices for generating an inhalable medium according to the some embodiments of the disclosure will now be described, with reference to the accompanying drawings. Referring to FIG. 1, there is shown an example of a device 1 for generating an inhalable medium. In broad outline, the device 1 volatilizes a liquid, which contains a wetting agent, to form a vapor or an aerosol which passes through a mixture of a solid basic material and a tobacco material so as to produce an inhalable medium that contains one or more constituents derived from the tobacco material.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A "colloid" is a substance in which microscopically dispersed insoluble particles are suspended throughout another substance.

Returning to FIG. 1, the device 1 of this example has a generally hollow cylindrical outer housing 2. The housing 2 has an open end 3. In this example, a tubular mouthpiece 4 is provided in the open end 3. The mouthpiece 4 in this example is removable by a user from the housing 2. An O-ring or other seal 5 assists in sealing the mouthpiece 4 in the housing 2. At or towards the other end 6 of the housing 2 is a battery 7 for powering various components of the device 1, as will be discussed further below. The battery 7 may be a rechargeable battery or a disposable battery. A controller 8 is also provided in the housing 2 for controlling the operation of various components of the device 1, as will be discussed further below.

The housing 2 has a container 9 for holding or containing a volatilizable material, which in this case is a liquid 10. The volatilizable material comprises a wetting agent, such as water. Various different forms for the container 9 may be used. In the example of FIG. 1, the container 9 is in the form of an annular chamber 9 provided in the housing 2 between the open end 3 and the other end 6. In this particular example, the housing 2 is in two parts, a first part 2a being towards the open end 3 and a second part 2b towards the other end 6. The first and second parts 2a,2b of the housing 2 may connect to each other via a screw thread, a bayonet fitting or the like. In use, a user can separate the first and second parts 2a,2b of the housing 2 to allow the liquid 10 to be replenished or replaced as necessary. Alternatively, the mouthpiece 4 can be removed to provide access to the container 9. It will be understood however that other arrangements are possible. For example, the liquid 10 may be provided in a discrete annular pot-like container which can be removed as a whole from the housing 2. Such a discrete container may be disposable so that the user replaces the liquid 10 by fitting a new container with liquid 10 in the housing 2. Alternatively, such a container may be reusable. In such a case, the user may replenish or replace liquid 10 in the container whilst it has been removed from the housing 2 and then replace the refilled container in the housing 2. It will be understood that the housing 2 need not be in two parts and that other arrangements enabling access for the user may be provided, for example, to enable refilling in situ.

A heater 11 is provided generally centrally of the housing 2, that is, centrally along the length and width of the housing 2 in this example. In this example, the heater 11 is powered by the battery 7 and is therefore electrically connected to the battery 7. The heater 11 may be an electrically resistive heater, including for example a nichrome resistive heater, a ceramic heater, etc. The heater 11 may be for example a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. Other heating arrangements may be used, including non-electrical heating arrangements.

This heater 11 is provided for volatilizing the liquid 10. In the example shown, an annular wick 12 surrounds the heater 11 and is in (thermal) contact with the heater 11. The outermost surface of the annular wick 12 is in contact with liquid 10 contained in the liquid container 9. The wick 12 is generally absorbent and acts to draw in liquid 10 from the liquid container 9 by capillary action. The wick 12 is preferably non-woven and may be for example a cotton or wool material or the like, or a synthetic material, including for example polyester, nylon, viscose, polypropylene or the like. Whilst this will be described more fully below, it may be noted here that in use, liquid 10 drawn into the wick 12 is heated by the heater 11. The liquid 10 may be volatilized so as to produce an aerosol of liquid droplets or sufficiently heated to produce a vapor. The aerosol or vapor so produced exits the wick 12 and passes towards the mouthpiece 4 as shown by the arrows A under the action of the user drawing on the mouthpiece 4. The heater 11 and wick 12 may be provided as a single, effectively integral item, sometimes referred to as an "atomizer", such that the heating and wicking is effectively carried out by a single unit.

The housing 2 further contains a chamber 13 which holds or contains a solid substrate 14 in the device 1. The substrate 14 is a granular mixture comprising a tobacco material and a solid basic material such as calcium carbonate. In use, a user can access the chamber 13 to replace or replenish the solid substrate 14 through the open end 3 of the housing 2 by removing the mouthpiece 4 and/or by separating the two parts 2a,2b of the housing 2. Various different forms for the chamber 13 may be used. For example, the chamber 13 may be a tube which is completely open at both ends and which contains the solid substrate 14. As another example, the chamber 13 may be a tube which has one or more end walls which have through holes through which a vapor or aerosol can pass. The chamber 13 may remain in situ within the housing 2 whilst the user removes and replaces the solid substrate 14. Alternatively, the chamber 13 containing the solid substrate 14 may be a discrete item which in use is inserted into and removed from the housing 2 as a whole. A removable chamber 13 of this type may be disposable so that the user replaces the solid substrate 14 by fitting a new chamber 13 containing fresh solid substrate 14 into the housing 2. As an alternative, the chamber 13 may be reusable. In such a case, the user may replace the solid substrate 14 in the chamber 13 whilst the chamber 13 has been removed from the housing 2 and then replace the refilled chamber 13 in the housing 2. In yet another example, the chamber 13 may comprise clips or the like provided internally of the housing 2 and which retain the solid substrate 14 in position. In some examples, the solid substrate 14 could simply fit snugly within the chamber 13. As another alternative, the container 9 for containing the liquid 10 may itself be arranged to support or carry the solid substrate 14. For example, the container 9 may have one or more clips or a tube or the like for receiving and holding the solid substrate 14 in position. Such a dual function container 9/chamber or receptacle 13 for both containing the liquid 10 and receiving the solid substrate 14 may be in the form of a cartridge or the like and may be a disposable item or may be re-useable, with the liquid 10 and solid substrate 14 being replaced or topped up by the user as required. In some cases, it may be that the user only needs to top up or replace the solid substrate 14 from time to time, with sufficient liquid 10 being provided for several uses. Once the liquid 10 has been consumed, the user disposes of the dual function container 9/receptacle 13 and uses a new one. Likewise, it may be that the user only needs to top up or replace the liquid 10 from time to time, with sufficient solid substrate 14 being provided for several uses. Once the solid substrate 14 has been consumed, the user disposes of the dual function container 9/receptacle 13 and uses a new one. Specific examples of dual function containers/receptacles are discussed further below.

The solid substrate 14 is located in the housing 2 downstream of the location where the aerosol or vapor is produced from the liquid 10 and upstream of the open end 3 of the housing 2 and the mouthpiece 4. In this particular example, the solid substrate 14 is effectively provided in the same portion or chamber of the housing 2 as the wick 12. The aerosol or vapor produced from the liquid 10 exits the wick 12 and passes as shown by the arrows A towards the solid substrate 14 under the action of the user drawing on the mouthpiece 4. In particular embodiments, the solid substrate 14 is porous so that the aerosol or vapor passes through the solid substrate 14 and then through the open end 3 of the housing 2 and the mouthpiece 4. The wetting agent, in aerosol or vapor form, contacts the solid basic material to form a basic solution. The base increases the tobacco pH, liberating nicotine which is then more readily entrained in the passing vapor/aerosol.

In some embodiments, the solid substrate 14 and/or its chamber 13 are arranged so that there is no air gap between the solid substrate 14/chamber 13 and the interior of the housing 2 so that the aerosol or vapor flows entirely through the solid substrate 14.

The liquid 10 is suitably a liquid that is volatilizable at reasonable temperatures, preferably in the range of 100-300° C. or more particularly around 150-250° C., as that helps to keep down the power consumption of the device 1. Suitable materials include those conventionally used in e-cigarette devices, including for example propylene glycol and glycerol (also known as glycerin).

The solid substrate 14 imparts a flavor to the aerosol or vapor produced from the liquid 10 as the aerosol or vapor passes through the solid substrate 14. As the aerosol or vapor passes through and over the solid substrate 14, the hot aerosol or vapor entrains organic and other compounds or constituents from the solid substrate 14 that lend tobacco its organoleptic properties, thus imparting the flavor to the aerosol or vapor as it passes to the mouthpiece 4.

In the example shown in FIG. 1, the only heat source for heating the solid substrate 14 in the device 1, which is required so as to generate the organic and other compounds or constituents from the solid substrate 14, is the hot aerosol or vapor produced from heating the liquid 10.

Figure 2:
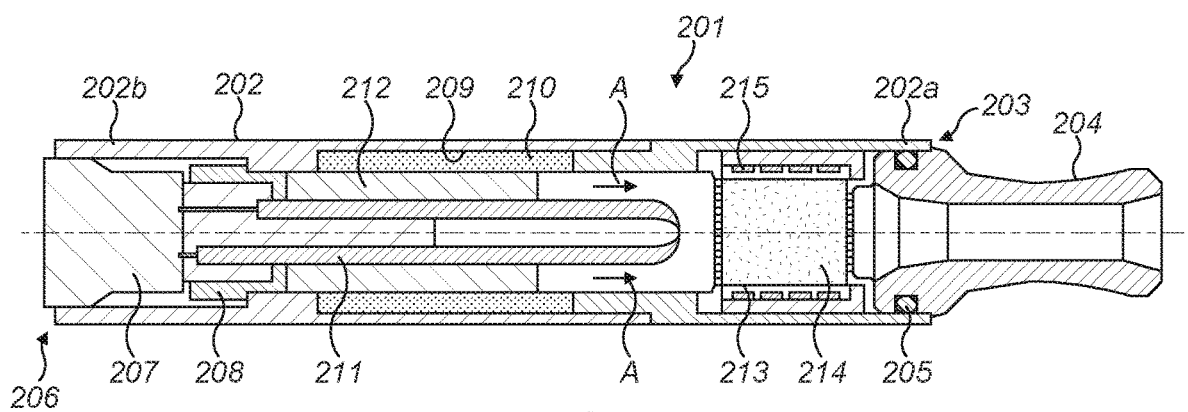
FIG. 2 shows a schematic longitudinal cross-sectional view of another example of a device for generating an inhalable medium.

Referring now to FIG. 2, there is shown another example of a device for generating an inhalable medium. In the following description and in FIG. 2, components and features that are the same as or similar to the corresponding components and features of the example described with reference to FIG. 1 have the same reference numeral but increased by 200. For the sake of brevity, the description of those components and features will not be repeated in its entirety here. It will be understood that the arrangements and alternatives, etc. described above in relation to the example of FIG. 1 are also applicable to the example of FIG. 2. Again, in broad outline, the device 201 of FIG. 2 heats a liquid to form a vapor or an aerosol which passes through a solid substrate 214 so as to produce an inhalable medium that contains one or more constituents derived from the solid substrate 214.

The device 201 of this example has a generally hollow cylindrical outer housing 202 with an open end 203 and a tubular mouthpiece 204. The mouthpiece 204 in this example is removable by a user from the housing 202 and an O-ring or other seal 205 assists in sealing the mouthpiece 204 in the housing 202. A battery 207 for powering various components of the device 201 and a controller 208 are provided at or towards the other end 206 of the housing 202. The housing 202 of this example is in two parts, a first part 202a being towards the open end 203 and a second part 202b towards the other end 206.

The housing 202 has a container 209 for holding or containing a first volatilizable material which in this case is a liquid 210. The volatilizable material comprises a wetting agent, such as water. The container 209 may be of any of the types described above in relation to the example of FIG. 1. A heater 211 is provided generally centrally (lengthwise and widthwise) of the housing 202 for volatilizing the liquid 210. In this example, the heater 211 is powered by the battery 207 and is therefore electrically connected to the battery 207. The heater 211 may be an electrically resistive heater, a ceramic heater, etc. The heater 211 may be for example a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. Other heating arrangements may be used, including inductive heating arrangements or non-electrical heating arrangements. An annular wick 212 surrounds the heater 211 and is in (thermal) contact with the heater 211. The outermost surface of the annular wick 212 is in contact with liquid 210 contained in the liquid container 209. The liquid 210 may be heated so as to produce an aerosol of liquid droplets or sufficiently heated to produce a vapor. The aerosol or vapor so produced exits the wick 212 and passes towards the mouthpiece 204 as shown by the arrows A under the action of the user drawing on the mouthpiece 204. The heater 211 and wick 212 may be provided as a single, effectively integral item such that the heating and wicking is effectively carried out by a single unit.

The housing 202 further contains a chamber 213 which holds or contains a solid substrate 214 in the device 201. The substrate 24 is a granular mixture comprising a tobacco material and a solid basic material such as calcium carbonate. The chamber 213 may be of any of the types described above in relation to the example of FIG. 1. The solid substrate 214 is located in the housing 202 downstream of the location where the aerosol or vapor is produced from the liquid 210 and upstream of the open end 203 of the housing 202 and the mouthpiece 204. In this particular example, solid substrate 214 is effectively provided in the same portion or chamber of the housing 202 as the wick 212. The aerosol or vapor produced from the liquid 210 exits the wick 212 and passes as shown by the arrows A towards the solid substrate 214 under the action of the user drawing on the mouthpiece 204. In particular embodiments, the solid substrate 214 is porous so that the aerosol or vapor passes through the solid substrate 214 and then through the open end 203 of the housing 202 and the mouthpiece 204. The wetting agent, in aerosol or vapor form, contacts the solid basic material to form a basic solution. The base increases the tobacco pH, liberating nicotine which is then more readily entrained in the passing vapor/aerosol.

In some embodiments, solid substrate 214 and/or its chamber 213 are arranged so that there is no air gap between the solid substrate 214/chamber 213 and the interior of the housing 202 so that the aerosol or vapor flows entirely through the solid substrate 214. As the aerosol or vapor passes through and over the solid substrate 214, the hot aerosol or vapor entrains organic and other compounds or constituents from the solid substrate 214 that lend tobacco its organoleptic properties, thus imparting the flavor to the aerosol or vapor as is passes to the mouthpiece 204.

The container 209 for containing the liquid 210 may itself be arranged to support or carry the solid substrate 214. For example, the container 209 may have one or more clips or a tube or the like for receiving and holding the solid substrate 214 in position. Such a dual function container 209/chamber or receptacle 213 for both containing the liquid 210 and receiving the solid substrate 214 may be in the form of a cartridge or the like and may be a disposable item or may be re-useable, with the liquid 210 and solid substrate 214 being replaced or topped up by the user as required. In some cases, it may be that the user only needs to top up or replace the solid substrate 214 from time to time, with sufficient liquid 210 being provided for several uses. Once the liquid 210 has been consumed, the user disposes of the dual function container 209/receptacle 213 and uses a new one. Likewise, it may be that the user only needs to top up or replace the liquid 210 from time to time, with sufficient solid substrate 214 being provided for several uses. Once the solid substrate 214 has been consumed, the user disposes of the dual function container 209/receptacle 213 and uses a new one.

In the example device 201 of FIG. 2, a second heater 215, such as an oven heater, is provided in thermal contact with the solid substrate 214 to pre-heat the solid substrate 214 and/or provide additional heat to the solid substrate 214 throughout use of the device 201. This encourages release of constituents from the tobacco material as the vapor or aerosol passes through the solid substrate 214 in use. The amount of heated liquid 210 need to achieve desirable heating of the solid substrate 214 may be reduced. The second heater 215 may be an electrically resistive heater, a ceramic heater, etc., powered by for example the battery 207. The second heater 215 may be for example a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. The second heater 215 may be an inductive heater powered by for example the battery 207. Solid substrate 214 may include materials susceptible to inductive heating. Other heating arrangements may be used for the second heater 215, including non-electrical heating arrangements.

In the example device 201 of FIG. 2, the heater 215 for heating the solid substrate 214 is provided externally of the solid substrate 214 and heats the solid substrate 214 by heat conduction from the exterior of the solid substrate 214. The heater 215 in this example is generally cylindrical. The heater 215 may in effect be an integral part of the device 201 and be provided as part of the housing 202. As an alternative, the heater 215 may be provided integrally with the chamber 213 which holds or contains the solid substrate 214. In this alternative, in the case that the chamber 213 is disposable, the heater 215 will be replaced when a new chamber 213 with fresh solid substrate is loaded into the device 201 by the user.

Figure 3:
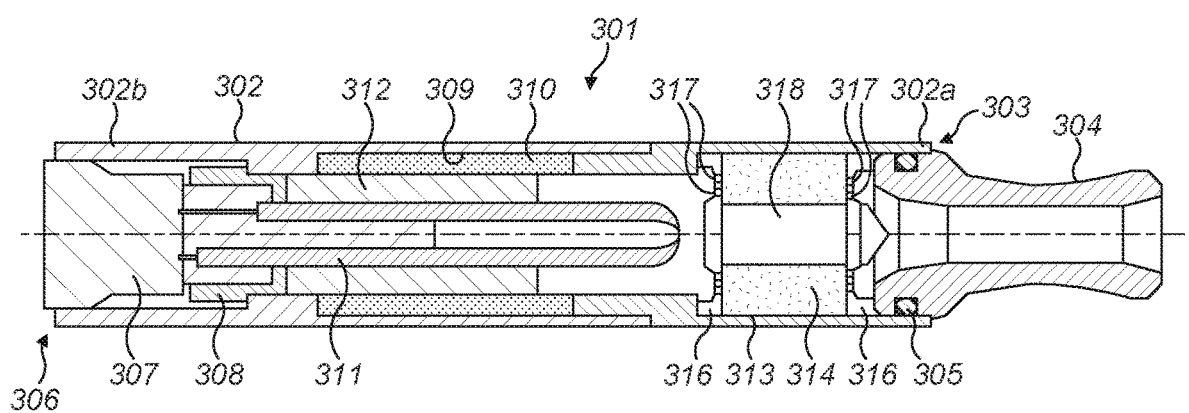
FIG. 3 shows a schematic longitudinal cross-sectional view of another example of a device for generating an inhalable medium.

Referring now to FIG. 3, there is shown another example of a device for generating an inhalable medium. In the following description and in FIG. 3, components and features that are the same as or similar to the corresponding components and features of the example described with reference to FIG. 1 have the same reference numeral but increased by 300. For the sake of brevity, the description of those components and features will not be repeated in its entirety here. It will be understood that the arrangements and alternatives, etc. described above in relation to the examples of FIG. 1 and FIG. 2 are also applicable to the example of FIG. 3. Again, in broad outline, the device 301 of FIG. 3 heats a liquid to form a vapor or an aerosol which passes through a solid substrate 314 so as to produce an inhalable medium that contains one or more constituents derived from the solid substrate 314.

The device 301 of this example again has a generally hollow cylindrical outer housing 302 with an open end 303 and a tubular mouthpiece 304, which is removable by a user from the housing 302. O-ring or other seal 305 assists in sealing the mouthpiece 304 in the housing 302. A battery 307 for powering various components of the device 301 and a controller 308 are provided at or towards the other end 306 of the housing 302. The housing 302 of this example is again in two parts, a first part 302a being towards the open end 303 and a second part 302b towards the other end 306.

The housing 302 has a container 309 for holding or containing a volatilizable material, which in this case is a liquid 310 The volatilizable material comprises a wetting agent, such as water. The container 309 may be of any of the types described above in relation to the examples of FIGS. 1 and 2. A heater 311 is provided generally centrally of the housing 302 for heating the liquid 310. The heater 311 may be any of the types described above. In this example, the heater 311 is powered by the battery 307 and is therefore electrically connected to the battery 307. An annular wick 312 surrounds the heater 311 and is in (thermal) contact with the heater 311. The outermost surface of the annular wick 312 is in contact with liquid 310 contained in the liquid container 309. The liquid 310 may be heated so as to produce an aerosol of liquid droplets or sufficiently heated to produce a vapor. The aerosol or vapor so produced exits the wick 312 and passes towards the mouthpiece 304 as shown by the arrows A under the action of the user drawing on the mouthpiece 304. The heater 311 and wick 312 may be provided as a single, effectively integral item such that the heating and wicking is effectively carried out by a single unit.

The housing 302 further contains a chamber 313 which holds or contains a solid substrate 314 in the device 301. The substrate 314 is a granular mixture comprising a tobacco material and a solid basic material such as calcium carbonate. The chamber 313 may be of any of the types described above in relation to the examples of FIGS. 1 and 2. (In the example shown in FIG. 3, the chamber 313 is in the form of a tube which has end walls 316 which have through holes 317 through which a vapor or aerosol can pass, which was mentioned as an option above.) The solid substrate 314 is located in the housing 302 downstream of the location where the aerosol or vapor is produced from the liquid 310 and upstream of the open end 303 of the housing 302 and the mouthpiece 304. In this particular example, again, the solid substrate 314 is effectively provided in the same portion or chamber of the housing 302 as the wick 312. The aerosol or vapor produced from the liquid 310 exits the wick 312 and passes as shown by the arrows A towards the solid substrate 314 under the action of the user drawing on the mouthpiece 304. In particular embodiments, the solid substrate 314 is porous so that the aerosol or vapor passes through the solid substrate 314 and then through the open end 303 of the housing 302 and the mouthpiece 304. The wetting agent, in aerosol or vapor form, contacts the solid basic material to form a basic solution. The base increases the tobacco pH, liberating nicotine which is then more readily entrained in the passing vapor/aerosol.

In some embodiments, the solid substrate 314 and/or its chamber 313 are arranged so that there is no air gap between the solid substrate 314/chamber 313 and the interior of the housing 302 so that the aerosol or vapor flows entirely through the solid substrate 314. As the aerosol or vapor passes through and over the solid substrate 314, the hot aerosol or vapor entrains organic and other compounds or constituents from the solid substrate 314, thus imparting tobacco flavor to the aerosol or vapor as is passes to the mouthpiece 304. The container 309 for containing the liquid 310 may itself be arranged to support or carry the solid substrate 314. For example, the container 309 may have one or more clips or a tube or the like for receiving and holding the solid substrate 314 in position. Such a dual function container 309/chamber or receptacle 313 for both containing the liquid 310 and receiving the solid substrate 314 may be in the form of a cartridge or the like and may be a disposable item or may be re-useable, with the liquid 310 and solid substrate 314 being replaced or topped up by the user as required. In some cases, it may be that the user only needs to top up or replace the solid substrate 314 from time to time, with sufficient liquid 310 being provided for several uses. Once the liquid 310 has been consumed, the user disposes of the dual function container 309/receptacle 313 and uses a new one. Likewise, it may be that the user only needs to top up or replace the liquid 310 from time to time, with sufficient solid substrate 314 being provided for several uses. Once the solid substrate 314 has been consumed, the user disposes of the dual function container 309/receptacle 313 and uses a new one.

In the example device 301 of FIG. 3, a second heater 318 is again provided in thermal contact with the solid substrate 314 to heat the solid substrate 314 to encourage release of constituents from the solid substrate 314 as the vapor or aerosol passes through the solid substrate 314 in use. The second heater 318 may be an electrically resistive heater, a ceramic heater, etc., powered by for example the battery 307. Other heating arrangements may be used for the second heater 318, including non-electrical heating arrangements.

In the example device 301 of FIG. 3, the heater 318 for heating the solid substrate 314 is provided internally of the solid substrate 314 and heats the solid substrate 314 by heat conduction from the interior of the solid substrate 314. The heater 318 in this example is generally in the form of a cylindrical rod located along the central longitudinal axis of the solid substrate 314. In other arrangements, the heater 318 may be a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. The solid substrate 314 in this case is generally tubular or otherwise has an internal aperture for receiving the heater 318. The heater 318 may in effect be an integral part of the device 301 and be provided as part of the housing 302. In this case, as the solid substrate 314 is loaded into the device 301 (for example, as the chamber 313 containing the solid substrate 314 is loaded into the device 301), the solid substrate 314 surrounds the second heater 318. As an alternative, the heater 318 may be provided integrally with the chamber 313 which holds or contains the solid substrate 314. In this alternative, in the case that the chamber 313 is disposable, the heater 318 will be replaced when a new chamber 313 with fresh tobacco is loaded into the device 301 by the user.

In another example, plural internal heaters 318 may be provided, so as to provide for more efficient heating of the solid substrate 314. In another example, the solid substrate 314 may be heated by both one or more external heaters (like the second heater 215 of the example of FIG. 2) and by one or more internal heaters (like the second heater 318 of the example of FIG. 3).

Figure 4:
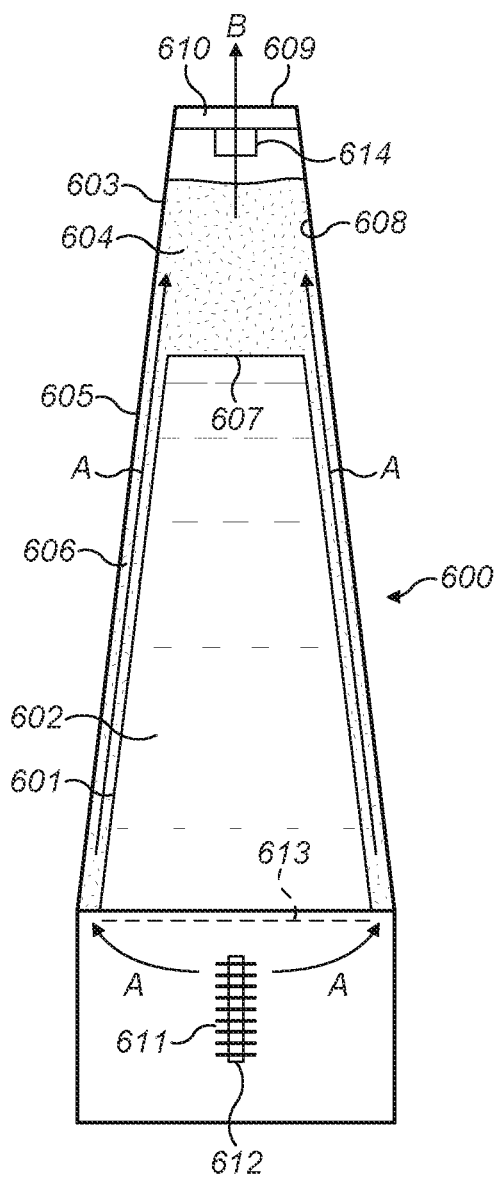

Referring now to FIG. 4, there is shown a schematic longitudinal cross-sectional view of an example of a cartridge 600 having a first container 601 which holds a first volatilizable material, which in this case is a liquid 602 including a wetting agent such as water, and a receptacle or container 603 for solid substrate 604. The substrate 604 is a granular mixture comprising a tobacco material and a solid basic material such as calcium carbonate. In this example, the first container 601 and the solid substrate container 603 are provided as one integral component, either by being formed integrally initially or being formed initially of two parts which are then assembled in a substantially permanent fashion. The cartridge 600 is arranged so that as the liquid 602 is volatilized so as to produce an aerosol of liquid droplets or sufficiently heated to produce a vapor, at least some and preferably all or substantially all of the aerosol or vapor passes through the solid substrate 604 to (i) contact and dissolve the solid basic material to form a basic solution which increases the tobacco pH and liberates nicotine, and (ii) pick up flavor and nicotine from the tobacco material.

In the example of FIG. 4, the first container 601 is provided generally centrally of the cartridge 600. The first container 601 in the example shown is frustoconical in shape, but may have a different shape, such as conical, cylindrical, etc. The first container 601 is surrounded by an outer shell 605 which defines an annular channel 606 around the outside of the length of the first container 601 and which extends from one end of the first container 601 to the other. The outer shell 605 extends beyond a first end wall 607 of the first container 601 to define a chamber 608 beyond the first end wall 607 of the first container 601. In the example shown, both the chamber 608 and the annular channel 606 contain the solid substrate 604 and so can be regarded as together providing the container 603 for the solid substrate 604. In other examples, the solid substrate 604 may be provided only in the chamber 608, which therefore defines the container 603 for the solid substrate 604, and the annular channel 606 is empty. The chamber 608 is closed off by an end wall 609 which is spaced from the end wall 607 of the first container 601. The end wall 609 may be part of the outer shell 605 or may be a separate plastics or rubber cap or the like. In yet other examples, the annular channel 606 contains the solid substrate 604 and there is no material in the chamber 608, and indeed the chamber 608 may be omitted and the channel 606 effectively terminates at the end wall 609. The channel 606 and/or chamber 608 may be entirely filled with solid substrate 604 or may only contain a portion or plug of solid substrate 604. The end wall 609 is porous and/or has one or more through holes 610 to enable the aerosol or vapor to exit the cartridge 600 to be inhaled by a user. The first container 601 and the solid container 603 may each be formed of rigid, watertight and airtight materials, such as metal, suitable plastics, etc.

The example cartridge 600 shown in FIG. 4 is provided with a heater 611 and a wick 612 in (thermal) contact with the heater 611. In this example, the heater 611 and the wick 612 are provided as a single unit, often referred to as an "atomizer". In this case, where the cartridge 600 includes an atomizer, such a cartridge is often referred to as a "cartomizer". The orientation of the heater 611 is shown schematically and for example the heater 611 may be a coil having its longitudinal axis perpendicular to the longitudinal axis of the cartridge 600 rather than parallel as shown in FIG. 4.

The wick 612 is in contact with the liquid 602. This may be achieved by for example the wick 612 being inserted through a through hole (not shown) in the second end wall 613 of the first container 601. Alternatively or additionally, the second end wall 613 may be a porous member (shown schematically in FIG. 4 by dashed lines) which allows liquid to pass through from the first container 601, and the wick 612 may be in contact with the porous second end wall 613. The second end wall 613 may be for example in the form of a porous ceramic disk. A porous second end wall 613 of this type helps to regulate the flow of liquid onto the wick 612. The wick 612 is generally absorbent and acts to draw in liquid 602 from the first container 601 by capillary action. The wick 612 is preferably non-woven and may be for example a cotton or wool material or the like, or a synthetic material, including for example polyester, nylon, viscose, polypropylene or the like.

In use, the cartridge 600 is connected by the user to a battery section of a device (not shown) to enable the heater 611 to be powered. When the heater 611 of the atomizer is powered (which may be instigated for example by the user operating a button of the overall device or by a puff detector of the overall device, as is known per se), liquid 602 drawn in from the first container 601 by the wick 612 is heated by the heater 611 to volatilize or vaporize the liquid. As the user draws on a mouthpiece of the overall device, the vapor or aerosol passes into the annular channel 606 around the outside of the length of the liquid container 601 and into the chamber 608 as shown by the arrows A. The vapor or aerosol picks up flavor and nicotine from the tobacco material in the solid substrate 604. The wetting agent, in aerosol or vapor form, contacts the solid basic material to form a basic solution. The base increases the tobacco pH, liberating nicotine which is then more readily entrained in the passing vapor/aerosol. The vapor or aerosol can then exit the cartridge 600 through the end wall 609 as shown by the arrow B. Optionally, a one way valve 614 may be provided inside the end wall 609 so that the vapor or aerosol can only exit the cartridge 600 and cannot back-flow to the heater 611 or the electronics of the device as a whole.

Figure 5:
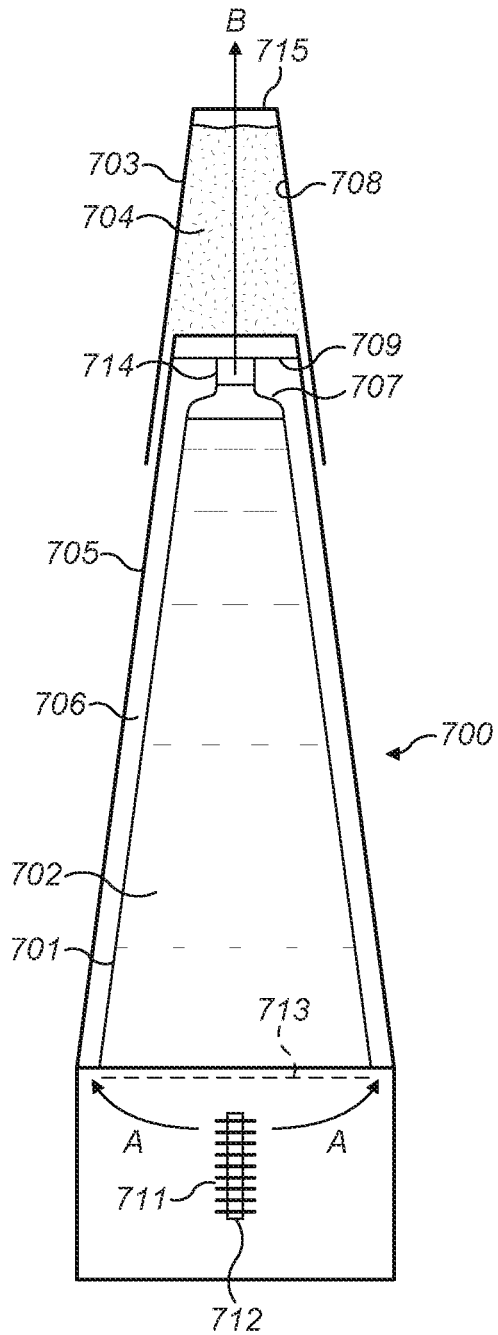
FIG. 5 shows a schematic longitudinal cross-sectional view of an example of a cartridge having a liquid container and a detachable container for solid material.

Referring now to FIG. 5, there is shown a schematic longitudinal cross-sectional view of another example of a cartridge 700 having a first container 701 which holds a first volatilizable material, which in this case is a liquid 702 including a wetting agent such as water, and a container 703 which defines a chamber 708 for containing solid substrate 704. The substrate 704 is a granular mixture comprising a tobacco material and a solid basic material such as calcium carbonate. In the following description and in FIG. 5, components and features that are the same as or similar to the corresponding components and features of the example described with reference to FIG. 4 have the same reference numeral but increased by 100. For the sake of brevity, the description of those components and features will not be repeated in its entirety here.

In this example, the first container 701 and the solid substrate container 703 of the cartridge 700 are provided as separate components, which are detachably connected to each other in use. The first container 701 and the solid substrate container 703 may for example be clipped or otherwise detachably fixed to each other, or for example the tobacco composition container 703 may simply rest on or be a tight friction fit on the first container 701. The cartridge 700 is arranged so that as the liquid 702 is volatilized so as to produce an aerosol of liquid droplets or sufficiently heated to produce a vapor, at least some and preferably all or substantially all of the aerosol or vapor passes through the solid substrate 704 to (i) contact and dissolve the solid basic material to form a basic solution which increases the tobacco pH and liberates nicotine, and (ii) pick up flavor and nicotine from the tobacco material.

In this example, the first container 701 is surrounded by an outer shell 705 which defines an annular channel 706 around the outside of the length of the first container 701 and which extends from one end of the first container 701 to the other. The outer shell 705 extends beyond a first end wall 707 of the first container 601 and terminates in an end wall 709. The end wall 709 may be a separate plastics or rubber cap or the like. The end wall 709 is porous and/or has one or more through holes 710 to enable the aerosol or vapor to exit the annular channel 706. A one way valve 714 may be provided inside the end wall 709 so that the vapor or aerosol can only exit the annular channel 706 at the end remote from the heater 711 and wick 712 and cannot back-flow to the heater 711 or the electronics of the device as a whole. The solid substrate container 703 is located in use over the end wall 709 so that vapor or aerosol exiting through the end wall 709 passed into the solid substrate container 703. The solid substrate container 703 has an exit aperture and/or or a porous end wall 715 to enable the aerosol or vapor to exit the cartridge 700 to be inhaled by a user.

In use, the cartridge 700 is connected by the user to a battery section of a device (not shown) to enable the heater 711 to be powered. When the heater 711 of the atomizer is powered (which may be instigated for example by the user operating a button of the overall device or by a puff detector of the overall device as is known per se), liquid 702 drawn in from the first container 701 through the end wall 713 by the wick 712 is heated by the heater 711 to volatilize or vaporize the liquid. As the user draws on a mouthpiece of the overall device, the vapor or aerosol passes into the annular channel 706 around the outside of the length of the first container 701 towards the end wall 709 of the outer shell 705 as shown by the arrows A. The vapor or aerosol then passes through the end wall 709 (via the one-way valve 714 if present) and into the solid substrate container 703 where it picks up flavor and nicotine from the tobacco material in the solid substrate 704 contained in the container 703. The wetting agent, in aerosol or vapor form, contacts the solid basic material to form a basic solution. The base increases the tobacco pH, liberating nicotine which is then more readily entrained in the passing vapor/aerosol. The vapor or aerosol can then exit the cartridge 700 through the end wall 715 of the solid substrate container 703 as shown by the arrow B.

The examples shown in FIGS. 4 and 5 are particularly suitable for use with so-called modular or "e-go" products, in which the cartomizer is fitted to a battery section (not shown), typically by a screw thread, a bayonet fitting or the like. The cartomizer as a whole is typically discarded after use and a new, replacement cartomizer used. As an alternative, it may be possible for the user to re-use the cartridge by refilling the liquid and/or replacing the solid material from time to time as necessary.

The examples shown in FIGS. 4 and 5 may easily be adapted for use with other types of an electronic tobacco hybrid device, which are known per se. There are for example so-called "look alike e-cigarette" or "cig-alike" devices which are generally small and have a form and appearance similar to a conventional cigarette. In such devices, the first container typically includes some wadding material, of for example cotton or the like, for holding a liquid. The cartridge or cartomizer in such known devices is typically disposable as a whole, but it may be possible to refill the liquid and/or replace the solid substrate in examples that use an embodiment of the present disclosure. As another example, there are so-called tank devices or personal vaporizers which generally have large liquid containers for holding relatively large volumes of liquid and also provide for advanced functions that allow users to control a number of aspects of the device.

As an alternative to any of the cartomizer arrangements discussed above, the atomizer (i.e. the heater and the wick) for the liquid may be provided separately of the liquid and tobacco containers. The atomizer may for example be provided as part of the battery section of the overall device to which the cartridge is detachably fitted by the user in use.

In any of the examples described above in relation to FIGS. 4 and 5, there may also be provided a heater for the solid substrate so as to "pre-heat" it. This heater may be provided as part of the cartridge or as part of the battery section of the device to which the cartridge is fitted in use.

As used herein, "aerosol generating agent" refers to a compound or mixture that promotes the generation of an aerosol. An aerosol generating agent may promote the generation of an aerosol by promoting an initial vaporization and/or the condensation of a gas to an inhalable solid and/or liquid aerosol.

In general, any suitable aerosol generating agent or agents may be included in the aerosol-generating article of the disclosure. Suitable aerosol generating agents include, but are not limited to: a polyol such as sorbitol, glycerol, and glycols like propylene glycol or triethylene glycol; a non-polyol such as monohydric alcohols, high boiling point hydrocarbons, acids such as lactic acid, glycerol derivatives, esters such as diacetin, triacetin, triethylene glycol diacetate, triethyl citrate or myristates including ethyl myristate and isopropyl myristate and aliphatic carboxylic acid esters such as methyl stearate, dimethyl dodecanedioate and dimethyl tetradecanedioate.

As used herein, the terms "flavor" and "flavoring" refer to materials which, where local regulations permit, may be used to create a desired taste or aroma in a product for adult consumers. They may include extracts (e.g., liquorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus *Mentha*), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

For the avoidance of doubt, where in this specification the term "comprises" is used in defining the invention or features of the invention, embodiments are also disclosed in which the invention or feature can be defined using the terms "consists essentially of" or "consists of" in place of "comprises".

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. An aerosol-generating article comprising;
(i) an aerosolizable material comprising nicotine;
(ii) a solid basic material; and
(iii) a wetting agent;
wherein the wetting agent is encapsulated and wherein a capsule is ruptured in use to release the wetting agent so that it may be combined with the solid basic material.

2. An aerosol-generating article according to claim 1, wherein the aerosolizable material comprises a tobacco material.

3. An aerosol-generating article according to claim 1, wherein the aerosolizable material and the solid basic material are provided as a mixture.

4. An aerosol-generating article according to claim 1, wherein the solid basic material comprises sodium hydroxide, potassium hydroxide, calcium hydroxide, sodium hydrogen carbonate, potassium hydrogen carbonate, sodium carbonate, potassium carbonate, calcium carbonate or mixtures thereof.

5. An aerosol-generating article according to claim 1, wherein the wetting agent comprises an aerosol generating agent and/or water.

6. An aerosol-generating article according to claim 5, wherein the wetting agent comprises water, glycerol, propylene glycol or a mixture thereof.

7. An aerosol-generating article according to claim 1, wherein the wetting agent is pumped into contact with the solid basic material.

8. An aerosol-generating assembly comprising an aerosol-generating article according to claim 1 and a heater.

9. An aerosol-generating assembly according to claim 8, the aerosol-generating assembly comprising:
a container retaining a first volatilizable material, the first volatilizable material comprising the wetting agent;
a heater for volatilizing the first volatilizable material held in the container;
a chamber containing a mixture of an aerosolizable material comprising nicotine, and a solid basic material; and
an outlet;
the arrangement being such that in use, the first volatilizable material comprising the wetting agent is volatilized by the heater to form a vapor and/or an aerosol, which passes through the chamber containing the aerosolizable material and the solid basic material, and entrains one or more constituents of the aerosolizable material, thereby forming an inhalable medium which passes through the outlet.

10. An aerosol-generating assembly according to claim 9, wherein the first volatilizable material comprises an aerosol generating agent.

11. An aerosol-generating assembly according to claim 9, wherein the first volatilizable material comprises a liquid or gel.

12. A kit comprising an aerosol-generating article according to claim 1 and a device for use in generating an inhalable medium, wherein the device comprises a heater.

13. A method of generating an inhalable medium comprising:
providing a wetting agent in encapsulated form;
rupturing a capsule to release the wetting agent and to combining the wetting agent with a composition, the composition comprising a solid basic material and an aerosolizable material comprising nicotine, to release nicotine from the aerosolizable material, and
volatilizing components of the aerosolizable material to form an inhalable medium.

14. A method of providing sustained release of nicotine from an aerosolizable material comprising nicotine, the method comprising;
providing a wetting agent and a composition comprising a solid basic material and the aerosolizable material;
combining the wetting agent and the composition, thereby forming a basic solution; and liberating nicotine from the aerosolizable material.

15. The method according to claim 14, wherein the wetting agent is contacted with the solid basic material and the aerosolizable material, resulting in the release of nicotine from the aerosolizable material, wherein components of the aerosolizable material are volatilized to form an inhalable medium.

16. A cartridge for use in a device for containing an inhalable medium, the cartridge containing a solid basic material and an aerosolizable material comprising nicotine, wherein the cartridge is configured for use in a device which contains a reservoir of a wetting agent configured to release the wetting agent from the reservoir so that the wetting agent may be combined with the solid basic material.

17. An aerosol-generating article according to claim 1, wherein the aerosolizable material and the solid basic material are provided as a mixture.

\* \* \* \* \*